(12) United States Patent
Miller et al.

(10) Patent No.: US 9,393,395 B2
(45) Date of Patent: Jul. 19, 2016

(54) TATTOO MACHINE

(71) Applicants: Michael Chen, Baldwin Park, CA (US); Wen Wei, Baldwin Park, CA (US); Billy Chen, Baldwin Park, CA (US)

(72) Inventors: Adam Carl Miller, Los Angeles, CA (US); Igor Evguenievich Chak, West Hollywood, CA (US)

(73) Assignees: Michael Chen, Bladwin Park, CA (US); Wen Wei, Baldwin Park, CA (US); Billy Chen, Baldwin Park, CA (US)

( * ) Notice: Subject to any disclaimer, the term of this patent is extended or adjusted under 35 U.S.C. 154(b) by 208 days.

(21) Appl. No.: 14/160,069

(22) Filed: Jan. 21, 2014

(65) Prior Publication Data

US 2015/0202420 A1 Jul. 23, 2015

(51) Int. Cl.
*A61M 37/00* (2006.01)
*A01K 11/00* (2006.01)

(52) U.S. Cl.
CPC .......... *A61M 37/0076* (2013.01); *A01K 11/005* (2013.01); *A61M 2202/0468* (2013.01); *A61M 2205/10* (2013.01); *A61M 2205/33* (2013.01)

(58) Field of Classification Search
CPC ............ A61M 37/0076; A61M 37/0084; A01K 11/005; F16F 2222/06; F16F 9/53; F16F 9/56; F16F 9/50; F16F 9/5126; F16F 15/05; F16F 15/03
USPC ............................................ 606/186; 81/9.22
See application file for complete search history.

(56) References Cited

U.S. PATENT DOCUMENTS

| | | | | |
|---|---|---|---|---|
| 2,588,623 A * | 3/1952 | Eliscu | ............... | A61M 37/0076 604/47 |
| 4,031,783 A * | 6/1977 | Paul | ......................... | B26F 1/34 81/9.22 |
| 4,204,438 A | 5/1980 | Binaris et al. | | |
| 4,582,060 A * | 4/1986 | Bailey | ............... | A61M 37/0076 101/19 |
| 4,782,725 A * | 11/1988 | Spaulding | ......... | A61M 37/0084 30/362 |
| 4,914,988 A * | 4/1990 | Chang | .................. | A01K 11/005 606/186 |
| 5,279,552 A * | 1/1994 | Magnet | ............. | A61M 37/0076 604/47 |
| 5,471,102 A | 11/1995 | Becker et al. | | |
| 5,551,319 A | 9/1996 | Spaulding et al. | | |
| 5,741,290 A * | 4/1998 | Hsieh | ................ | A61M 37/0076 606/185 |
| 7,207,242 B1 | 4/2007 | Daigle | | |
| 7,340,980 B2 * | 3/2008 | Conti Vecchi | .... | A61M 37/0084 606/186 |

(Continued)

OTHER PUBLICATIONS

Manual for Dragonfly Tattoo Machine (http://www.inkmachines.com/sites/default/files/Manual_For_Dragonfly_tattoo_machine_ENG2.pdf).

(Continued)

*Primary Examiner* — Christopher L Templeton
(74) *Attorney, Agent, or Firm* — Rankin, Hill & Clark LLP

(57) ABSTRACT

A tattoo machine for oscillating a tattoo needle includes a main housing and a motor secured to the main housing. A needle bar member is movably secured to the main housing for linear oscillation relative thereto. A drive mechanism is operatively connected to an output shaft of the motor and to the needle bar member for translating rotary movement of the output shaft into linear oscillation of the needle bar member.

13 Claims, 6 Drawing Sheets

(56) References Cited

U.S. PATENT DOCUMENTS

| | | | |
|---|---|---|---|
| 7,518,479 B2 | 4/2009 | Mask et al. | |
| 8,522,647 B1* | 9/2013 | Dixon | A61M 37/0076 30/362 |
| 2003/0195542 A1* | 10/2003 | Lee | A61M 37/0076 606/186 |
| 2004/0116953 A1* | 6/2004 | Dixon | A61M 37/0076 606/186 |
| 2005/0028647 A1 | 2/2005 | Sloan | |
| 2007/0039791 A1* | 2/2007 | Krefeld | F16F 9/48 188/316 |
| 2008/0078271 A1 | 4/2008 | Atkinson | |
| 2008/0306502 A1 | 12/2008 | Lisec | |
| 2009/0183602 A1 | 7/2009 | Crockett | |
| 2010/0036317 A1 | 2/2010 | Ogginski et al. | |
| 2010/0191268 A1* | 7/2010 | Lee | A61M 37/0084 606/185 |
| 2010/0192730 A1 | 8/2010 | Dubin | |
| 2011/0048174 A1* | 3/2011 | Lin | A61M 37/0084 81/9.22 |
| 2011/0146453 A1 | 6/2011 | Forth | |

OTHER PUBLICATIONS

The Stigma-Rotary F.A.Q. (http://www.stigma-rotary-tattoo.com/cms/faq.html).

* cited by examiner

TATTOO MACHINE

BACKGROUND

The present disclosure generally relates to a tattoo machine. As is well known, tattoo machines are used to place ink below the surface of an object or article (e.g., a person's skin). In particular, a pin or needle punctures the surface and places the ink below the surface. When the surface is skin of a living being, the ink is placed at such a level in the skin where it remains permanently. Because the ink is permanent, an important design consideration for the tattoo machine is that it be able to position the needle precisely and that it be controlled precisely when the needle punctures the surface. Generally, the needle can reciprocate back and forth to puncture the surface and this motion is preferably limited in a direction perpendicular to the axis of the reciprocating motion.

Tattoo machines having a reciprocating shaft are well known. Some existing units use an open, mechanical make-and-break electrical contact system, which drives an electromechanical operated pivot arm. This, in turn, vibrates up and down. Other versions use electric motors with eccentric cams to drive an arm up and down. The make-and-break units typically have visible sparking contacts and may produce a high degree of noise when in use. Both types of machines may require constant adjustment due to changes and wear of any resilient components (e.g., springs). Other drawbacks associated with conventional tattoo machines include the lack of precise control of the reciprocating needle bar and the lack of an easy and inexpensive way to clean the tattoo machine between uses without damaging electrical components thereof, etc.

SUMMARY

According to one aspect, a tattoo machine for oscillating a tattoo needle includes a main housing and a motor secured to the main housing. A needle bar member is movably secured to the main housing for linear oscillation relative thereto. A drive mechanism is operatively connected to an output shaft of the motor and to the needle bar member for translating rotary movement of the output shaft into linear oscillation of the needle bar member.

According to another aspect, a method of dampening a tattoo machine is provided. More particularly, in accordance with the method, a main housing, a motor and a needle bar member are provided. The motor is secured to the main housing. The needle bar member is movably secured to the main housing for linear oscillation relative thereto. A drive mechanism is arranged on the main housing to translate rotary motion of an output shaft of the motor into linear oscillation of the needle bar member.

According to a further aspect, a tattoo machine includes a main housing, a motor removably attached to the main housing and a needle bar member movably secured to the main housing. The tattoo machine further includes a drive mechanism that translates rotary action from the motor into linear movement of the needle bar member. Also included are magnets for dampening linear movement of the needle bar member or removably attaching the motor to the main housing.

DETAILED DESCRIPTION

Figure 1:
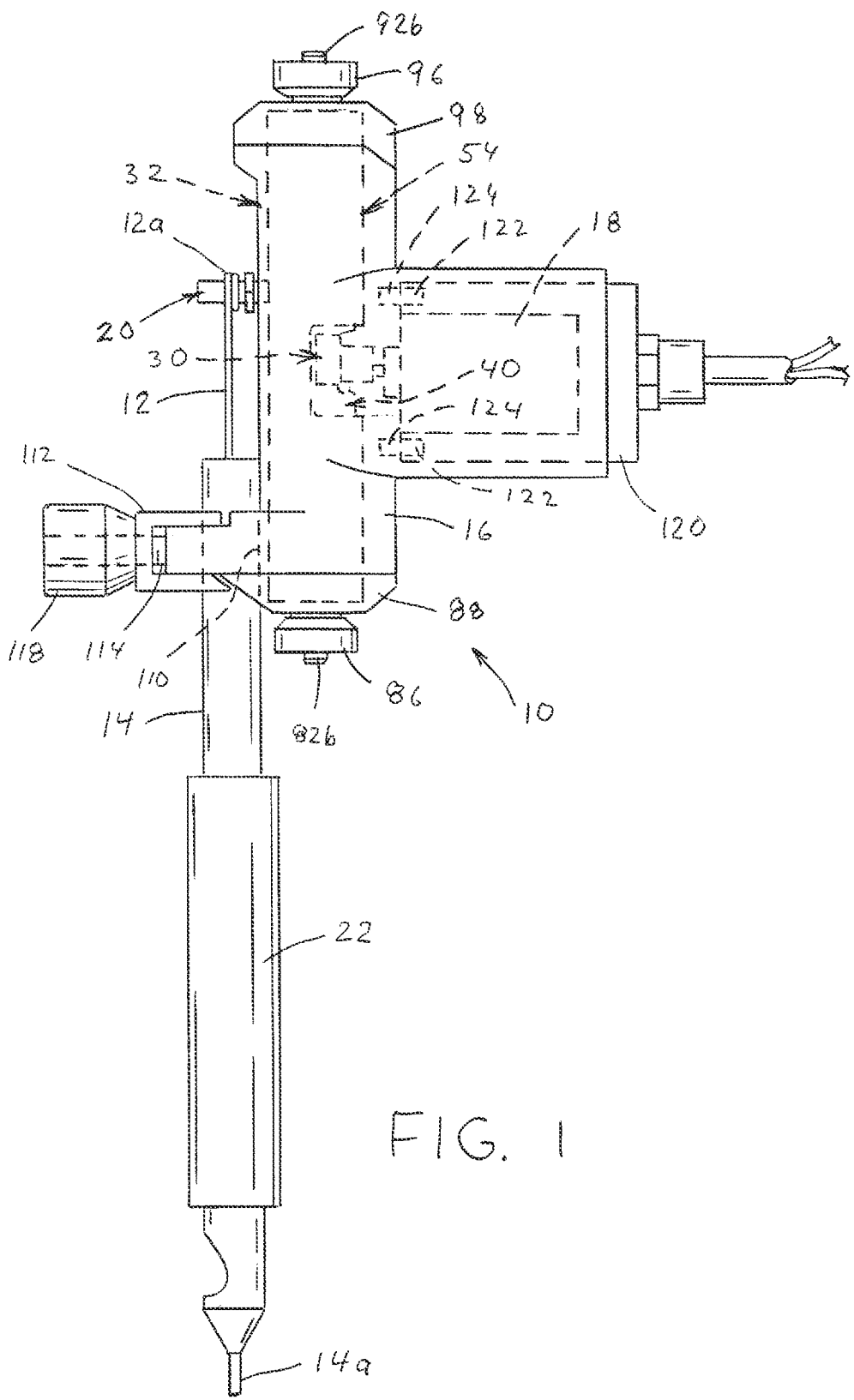
FIG. 1 is a side elevational view of a tattoo machine having a tattoo tube with a grip secured thereto and a tattoo needle received in the tube and connected to the tattoo machine for oscillation or reciprocating movement thereof.

Referring now to the drawings, wherein the showings are for purposes of illustrating one or more exemplary embodiments and not for purposes of limiting same, FIG. 1 illustrates a tattoo machine 10 for oscillating a tattoo needle 12 within a tattoo tube 14. As shown, the tattoo machine 10 includes a main housing 16 and a motor 18 secured to the main housing 16. In the particular embodiment illustrated, the motor 18 is removably attached to the main housing 16 as will be described in more detail below. Also as will be described in more detail below, the main housing 16 houses or encloses many movable components of the tattoo machine 10, but as will be appreciated and understood by those skilled in the art, the term housing is intended to broadly encompass any structure that encloses (fully or partially), surrounds or otherwise provides structure for such moving components, which would include an open frame or partial housing or enclosure.

A needle bar member 20 is movably secured to the main housing 16 for linear oscillation or reciprocation relative thereto. As shown, one end 12a of the needle 12 can be secured to the needle bar member 20 for translating the oscillation or reciprocating motion of the needle bar member 20 to the needle 12. Both the needle bar member 20 and the needle 12 move relative to the housing 16 and relative to the tattoo tube 14 temporarily fixedly secured to the housing 16. As is known by those skilled in the art, the tube 14 can be provided with a grip 22, which can be integrally formed with the tube or can be separately formed and thus be removable from the tube 14. The grip 22 allows a user of the tattoo machine 10 to precisely control the location of a tip end 14a of the tube out of which the needle 12 repeatedly projects as the needle 12 is reciprocated by the needle bar member 20.

A drive mechanism 30, 32 is operatively connected to an output shaft 26 of the motor 18 and to the needle bar member 20 for translating rotary movement of the output shaft 26 into linear oscillation or reciprocation of the needle bar member 20. Thus, the drive mechanism 30, 32 translates rotary action from the motor 18 into linear movement of the needle bar member 20. Optionally, and as will be described in more detail below, the tattoo machine 10 can include magnets for dampening linear movement of the needle bar member 20 and/or removably attaching the motor 18 to the main housing 16. In the illustrated embodiment, and again as will be described in more detail below, magnets are used for both dampening linear movement of the needle bar member 20 and removably attaching the motor 18 to the main housing 16.

Figure 2:
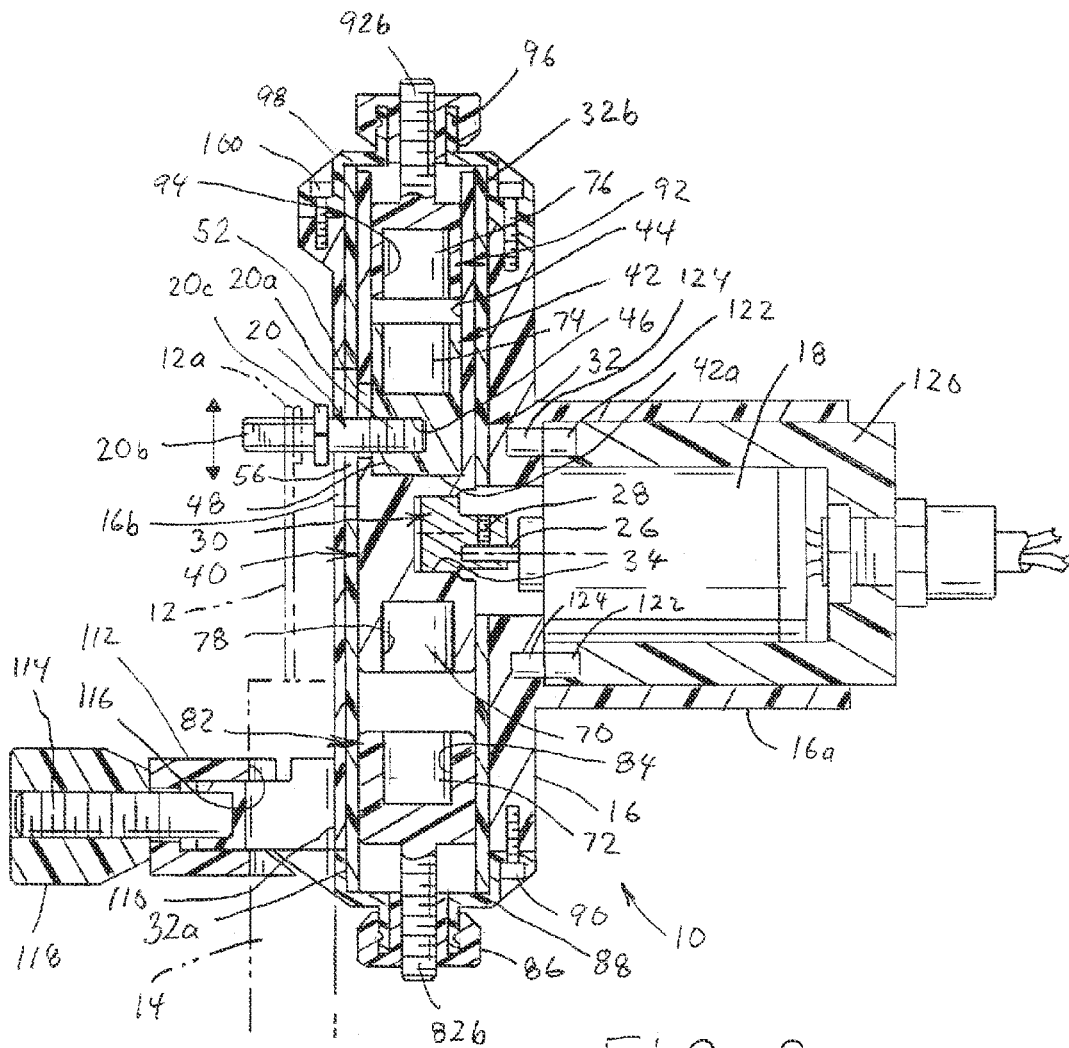
FIG. 2 is a cross-sectional view of the tattoo machine of FIG. 1.
Figure 3:
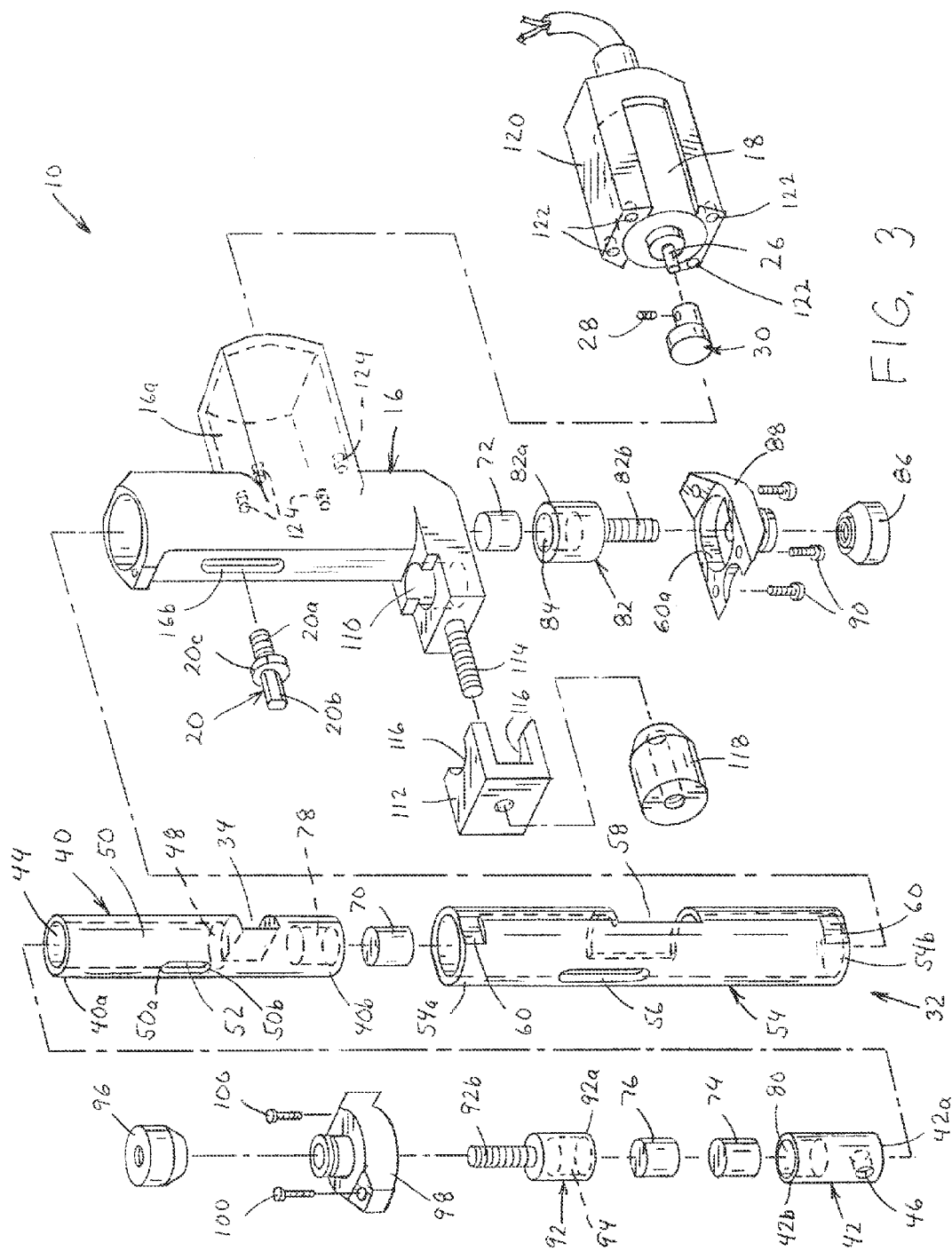
FIG. 3 is an exploded perspective view of the tattoo machine of FIG. 1.

With additional reference to FIGS. 2 and 3, the drive mechanism 30, 32 of the illustrated tattoo machine 10 includes an eccentric member 30 and a cartridge 32. The eccentric member 30 is fixed to the output shaft 26 of the motor 18 for rotation therewith, such as by illustrated set screw 28. The cartridge 32 is operatively connected to the needle bar member 20 and has a cutout portion or slot 34 defined therein for complementarily receiving the eccentric member 30 such that rotary movement of the eccentric member 30 linearly oscillates or reciprocates the cartridge 32, or at least a portion or parts thereof, and thereby the needle bar member 20. In particular, the eccentric member 30 is fixedly secured to the output shaft 26 such that rotation of the output shaft 26 causes corresponding rotation of the eccentric member 30. By this arrangement, rotation of the eccentric member 30 within the slot 34 causes the cartridge 32, or at least portions or parts thereof, to linearly oscillate or reciprocate along a longitudinal axis thereof as the rotary shaft 26 is rotated by the motor 18. While the illustrated embodiment employs drive mechanism 30, 32, it is to be appreciated by those skilled in the art that the drive mechanism need not be exactly as shown and/or described herein and can be any drive mechanism suitable for translating rotary action of a motor into linear oscillation or reciprocation of a tattoo needle.

The cartridge 32 of the illustrated embodiment includes a primary piston 40 having the slot 34 defined therein and a secondary piston 42 slidably and nestably received within an axial recess 44 defined within one end 40a of the primary piston 40. The needle bar member 20 is fixed or fixedly secured to the secondary piston 42 for synchronized movement therewith. That is, the linear oscillation or reciprocating movement occurs in tandem between the secondary piston 42 and the needle bar member 20. In the specific embodiment illustrated, the needle bar member 20 includes a threaded end 20a and a needle attaching end 20b, the ends 20a, 20b separated by a radial flange 20c that limits radial movement or insertion of the needle bar member 20 into the housing 16. The threaded end 20a is threadedly received in a threaded hole or aperture 46 defined radially into the secondary piston 42 to thereby fixedly secure the needle bar member 20 to the secondary piston 42. By fixedly secured, this means the parts 20 and 42 move integrally together, though the needle bar member 20 can be unthreaded from the aperture 46 if desired to disassemble the tattoo machine 10, and particularly to remove the needle bar member 20 from the cartridge 32.

The primary piston 40 includes a base wall 48 defining a depth of the axial recess 44. The base wall 48 abuts one end (e.g., lower end 42a) of the secondary piston 42 when the eccentric member 30 moves the primary piston 40 in a first direction (i.e., upward in FIG. 2) toward the secondary piston 42 and moves the secondary piston 42 in this first direction with the primary piston 40 (i.e., when moving upward, the primary piston 40 and the secondary piston 42 move together due to the abutment of the base wall 48 against the end 42a of the secondary piston 42). In contrast, the secondary piston 42 does not necessarily move in tandem with the primary piston 40 when the primary piston 40 is driven by the eccentric member 30 in a second, opposite direction (i.e., down in FIG. 2).

In the illustrated embodiment, the primary piston 40 includes a sidewall 50 that defines a circumference or outer dimension of the axial recess 44. The sidewall 50 also defines an axially oriented slot 52 through which at least one of the secondary piston 42 and the needle bar member 20 is received. In particular, in the illustrated embodiment, the threaded end 20a of the needle bar member 20 is received through the axially oriented slot 52 of the primary piston 40 and through a slot 16b defined in the housing 16, though this is not required. End portions 50a, 50b of the sidewall 50 defining the axially oriented slot 52 restrict or limit oscillating or reciprocating movement of the secondary piston 42 and the needle bar member 20, particularly relative to the primary piston 40. In particular, the end portions 50a, 50b serve as limit stops that limit relative movement of the secondary piston 42, and the needle bar member 20 fixedly secured thereto, relative to the primary piston 40.

The cartridge 32 of the illustrated embodiment further includes a sleeve member 54 in which the primary piston 40 is received. The sleeve member 54 can be fixedly secured to the housing 16 and thus the pistons 40, 42 move relative to the sleeve member 54 and the housing 16 (i.e., the pistons 40, 42 are the parts or portions of the cartridge 32 that move during operation of the machine 10). As shown, the sleeve member 54 can have an axially oriented sleeve slot 56 defined therein along which the axially oriented slot 52 defined in the primary piston 40 can slidably travel. The sleeve member 54 can also have or define a cut out portion 58 defined therein along which the slot 34 of the primary piston 40 slidably travels. As shown, the sleeve member 54 can have flat portions 60 defined adjacent respective ends 54a, 54b of the sleeve member 54 for allowing the sleeve member 54 to be installed into the main housing 16 and arranged relative thereto such that the sleeve member 54 does not rotate relative to the main housing 16. Advantageously, the cartridge 32, which in the illustrated embodiment comprises the primary piston 40, the secondary piston 42 and the sleeve member 54, is a compact unit or assembly that can be installed in a variety of housings, including the illustrated main housing 16 of the illustrated embodiment.

The tattoo machine 10 can additionally include a pair of magnets disposed axially within the main housing 16 at one end of the cartridge 32 for dampening oscillating movement of the cartridge 32, or at least of the pistons 40, 42, and thereby the needle bar member 20. In the illustrated embodiment of FIGS. 1-3, the machine 10 includes a first pair of magnets 70, 72 disposed axially within the main housing 16 at a lower end 32a of the cartridge 32, particularly the lower end 40b of the piston 40, and a second pair of magnets 74, 76 also disposed axially within the main housing 16, but disposed at an upper end 32b of the cartridge 32, particularly the upper end 42b of the secondary piston 42b. Both pairs of magnets 70, 72 and 74, 76 can be for dampening movement of the needle bar member 20. Specifically, the first pair of magnets 70, 72 can dampen extended movement of the needle bar member 20 (i.e., movement that causes the tattoo needle 12 to extend from the tattoo tube 14) and the second pair of magnets 74, 76 can dampen retracted movement of the needle bar member (i.e., movement that causes the tattoo needle 12 to retract into or toward the tattoo tube 14).

One or both pairs of magnets 70, 72 and 74, 76 can be adjustable for adjusting the amount of dampening applied to the cartridge 32, and particularly to the pistons 40, 42. In the tattoo machine 10 in the illustrated embodiment, both pairs of magnets 70, 72 and 74, 76 are adjustable. In particular, an axial distance is defined between the first pair of magnets 70, 72 when the cartridge 32 (or pistons 40, 42) is at rest and this axial distance is adjustable for adjusting the amount of dampening provided by the first pair of magnets 70, 72. Likewise, another axial distance is defined between the second pair of magnets 74, 76 when the cartridge 32 (or the pistons 40, 42) is at rest and this axial distance between the magnets 74, 76 is adjustable for adjusting the amount of dampening provided by the second pair of magnets 74, 76. Adjusting the axial distances between the respective pairs of magnets allows for dampening of the reciprocating needle bar member 20 to be adjustable and adjustably controlled. Moreover, unlike mechanical damping devises (e.g., springs), the dampening provided by the magnets does not deteriorate over time and/or eventually fail, thus improving the working life of the tattoo machine 10.

More specifically, and referring to the tattoo machine 10 of the illustrated embodiment, the first magnet 70 of the pair of magnets 70, 72 can be arranged for synchronized movement with the cartridge 32, and particularly with the primary piston 40 of the cartridge 32. The second magnet 72 of the first pair of magnets 70, 72 can be normally fixed relative to the main housing 16. In particular, the second magnet 72 is adjustably movable relative to the main housing 16 for adjusting the axial distance between the pair of magnets 70, 72, but generally or normally remains fixed relative to the main housing 16 during operation of the tattoo machine 10, including reciprocating movement of the needle bar member 20. Likewise, the first magnet 74 of the second pair of magnets 74, 76 is arranged for synchronized movement with the cartridge 32, and particularly with the secondary piston 42, and the second magnet 76 of the second pair of magnets 74, 76 is normally fixed relative to the main housing 16. Specifically, the second magnet 76 is adjustably movable relative to the main housing 16 for adjusting the axial distance between the second pair of magnets 74, 76, but generally or normally remains fixed relative to the main housing 16 during operation of the tattoo machine 10, including during reciprocating movement of the needle bar member 20.

In the specific tattoo machine 10 illustrated in FIGS. 1-3, the first magnet 70 of the first pair of magnets 70, 72 can be received within an axial recess 78 defined within a lower end 40b or the primary piston 40 that is opposite the end 40a. Likewise, the magnet 74 of the second pair of magnets 74, 76 can be received within an axial recess 80 defined within an upper end 42b of the secondary piston 42 that is opposite the end 42a. Both magnets 70, 74 can be fixedly secured to the respective pistons 40, 42, such as by a friction fit, adhesive or other known attachment type.

The second magnet 72 of the first pair of magnets 70, 72 can be fixedly secured to an adjusting member 82. In particular, the magnet 72 can be received within an axial recess 84 defined within an end 82a of the adjusting member 82 and fixed thereto by any suitable connection type, such as by a friction fit, adhesive, etc. A second, opposite end 82b can be threadedly engaged with an operating handle 86 that functions to allow adjustment of the position of the magnet 72. An end cap 88 can be secured to the main housing 16 at a lower end thereof for securing or holding the cartridge 32 within the main housing 16. The end cap 88 can have the operating handle 86 rotatably secured thereto and can include flats 60a for cooperating with flats 60 on the sleeve 58 and preventing relative rotation between the sleeve 58 and the housing 16. In addition, the threaded end 82b of the adjusting member 82 can be received through the end cap 88 such that rotation of the operating handle 86 causes the adjusting member 82 and the magnet 72 secured thereto to linearly move relative to the end cap 88 and relative to the cartridge 32 disposed within the main housing 16, and thus relative to the magnet 70. The end cap 88 can be secured to the main housing 16 via any suitable fastener, such as the illustrated screws 90.

Likewise, the magnet 76 of the second pair of magnets 74, 76 can be fixedly secured to an adjusting member 92. In particular, the magnet 76 can be received within an axial recess 94 defined within an end 92a of the adjusting member 92 and can be fixed thereto as described hereinabove in relation to the magnet 72. A second, opposite end 92b can be threadedly secured to an operating handle 96 that functions to allow adjustment of the position of the magnet 76. An end cap 98 can be secured to the main housing 16 at an upper end thereof for securing or holding the cartridge 32 within the main housing 16. The operating handle 96 can be rotatably secured to the end cap 98 such that threaded engagement between the adjusting member 92, and particularly the threaded end 92b, and the operating handle 96 allows for rotation of the operating handle 96 to adjustably move the magnet 76 relative to the main housing 16 and relative to the cartridge 32, and thus relative to the magnet 74. The end cap 98 can be secured to the main housing 16 via any suitable fastener, such as the illustrated screws 100, and can include flats (not shown) for cooperating with flats 60 at the upper end of the sleeve 58.

For holding the tattoo tube 14, the main housing 16 can additionally define an aperture 110 through which the tattoo tube 14 is received. An adjusting member 112 can be movably disposed on a threaded member 114 extending from the main housing 16 adjacent the aperture 110. The adjusting member 112 can include recesses 116 for complementarily receiving and engaging the tube 14 and bracing the tube 14 against the main housing 16, particularly a portion thereof defining the aperture 110. Adjustment of the adjusting member 112 can occur via an operating handle 118 threadedly received on the threaded member 114.

In addition, the main housing 16 can include a housing portion 16a in which the motor 18 is removably received. The motor 18 can be fixedly secured within a motor housing 120 that is removably secured to the main housing 16 inside the housing portion 16a thereby allowing the motor housing 120 and the motor 18 to be selectively detached from the main housing 16. In particular, in the illustrated embodiment, the motor housing 120 is removably secured to the main housing 16 by at least one magnetic connection. For example, as shown, the magnetic connection can include one or more magnets 122 secured to the motor housing 120 that can be magnetically connected to one or more magnets 124 secured to the main housing 16. Removal of the motor housing 120 and the motor 18 from the main housing 16 advantageously allows for cleaning of the tattoo machine 10 without damage to the motor 18.

Figure 4:
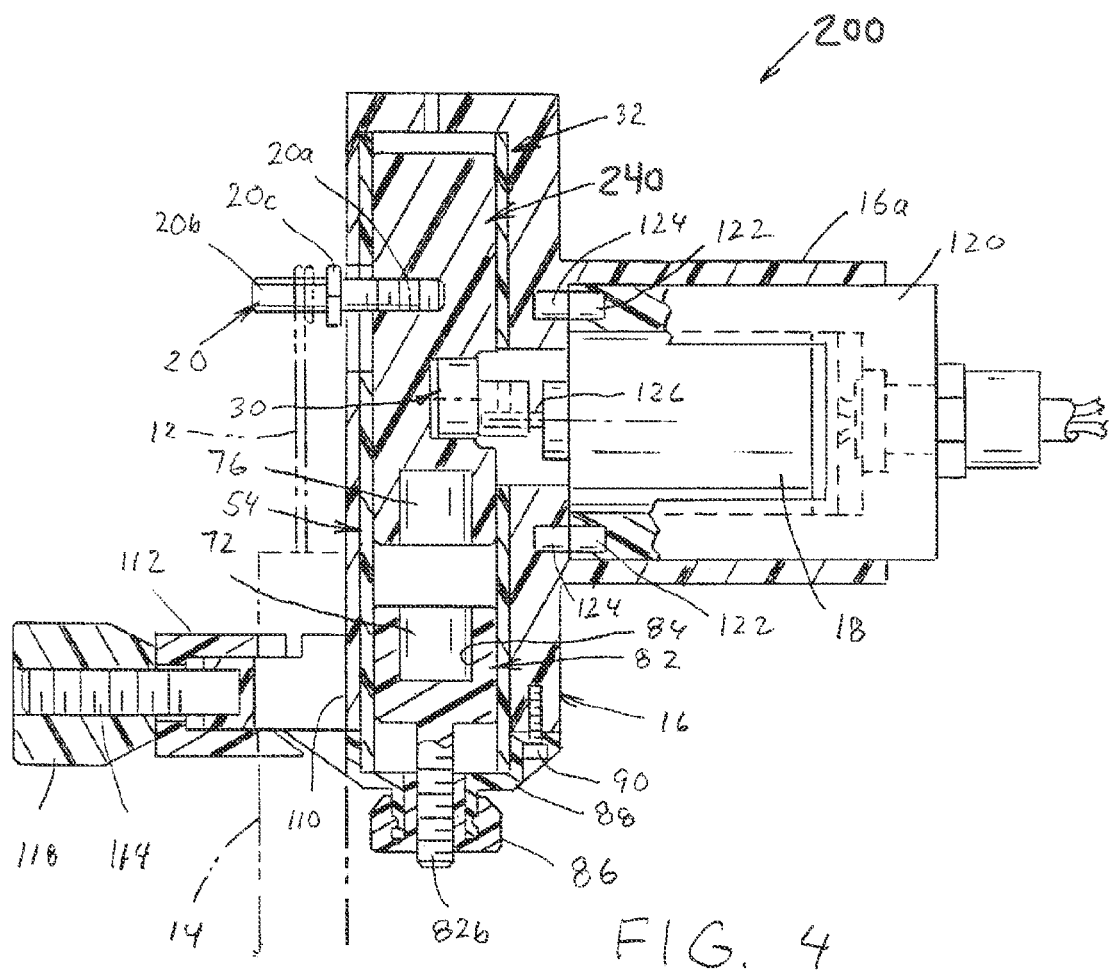
FIG. 4 is a cross-sectional view, similar to FIG. 2, but of a tattoo machine according to an alternate exemplary embodiment.

With reference now to FIG. 4, a tattoo machine 200 is shown according to an alternate exemplary embodiment. The tattoo machine 200 can be the same or similar to the tattoo machine 200 except as indicated below and thus like reference numbers are used on like components. A primary difference between the tattoo machine 200 and the tattoo machine 10 is that the tattoo machine 200 includes only a single pair of magnets disposed at a lower end of a piston 240 (i.e., no magnets are provided at the upper end of piston 240) and no secondary piston (e.g., secondary piston 42) is included. Without the secondary piston, the needle bar member 20 is fixed directly to the primary piston 240 for synchronized movement therewith. With only a single pair of magnets 72, 76, dampening by the magnets only occurs when the piston 240 and the needle bar member 20 move the tattoo needle 12 toward the extended position. In most if not all other aspects, the tattoo machine 200 can function like the tattoo machine 10 of FIGS. 1-3.

Figure 5:
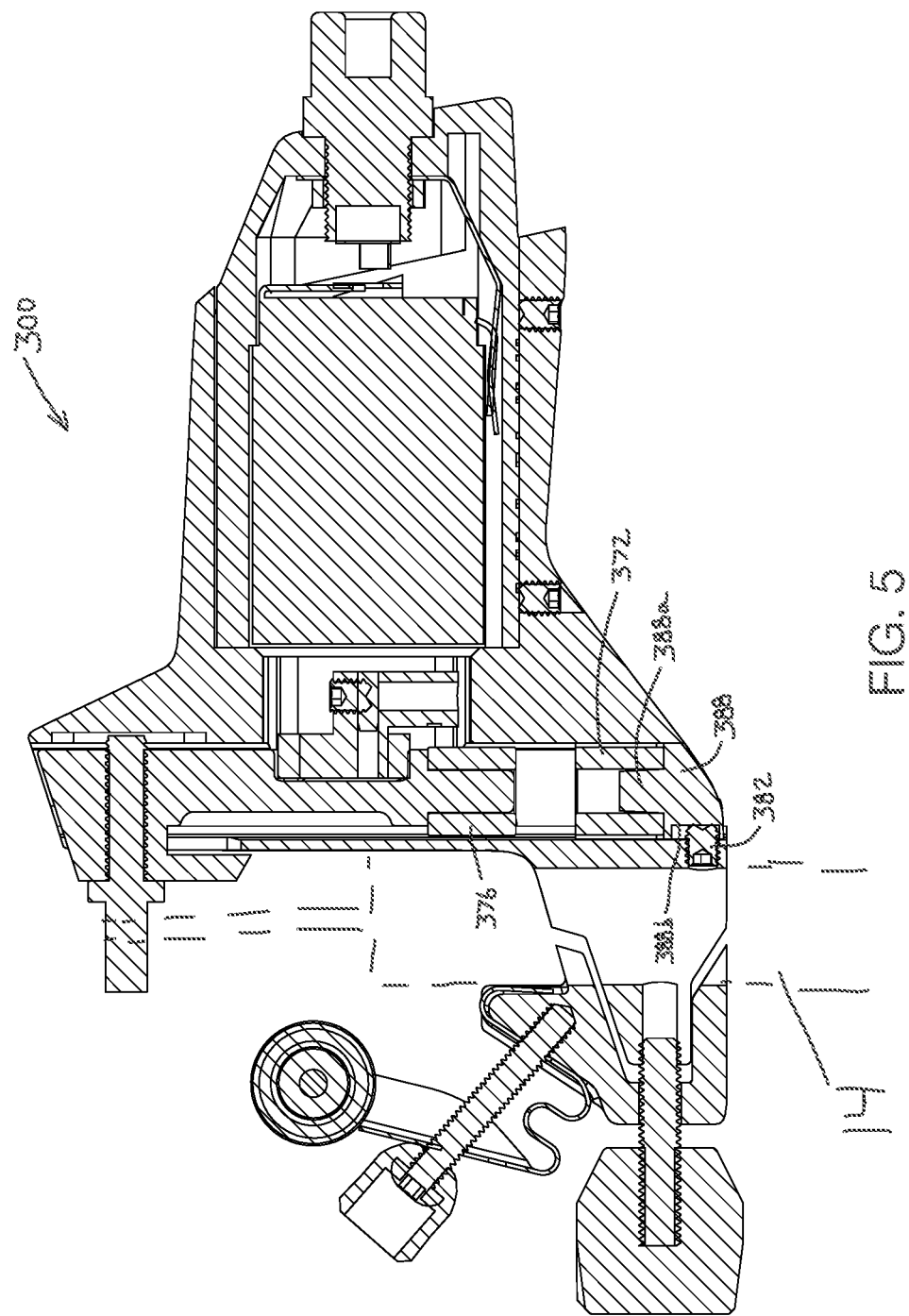
FIG. 5 is a cross-sectional view, similar to FIGS. 2 and 4, but of a tattoo machine according to another alternate exemplary embodiment.

With reference now to FIG. 5, a tattoo machine 300 is shown according to another alternate exemplary embodiment. The tattoo machine 300 can be the same or similar to the tattoo machine 200 except as indicated below. A primary difference between the tattoo machine 300 and the tattoo machine 200 is that the adjusting member 82, operating handle 86 and end cap 88 provided at the lower end of the tattoo machine 200 are replaced in the tattoo machine 300 with an end cap 388 that is only selectively adjustable (i.e., the end cap 388 cannot be adjusted when a tattoo tube 14 is installed on the tattoo machine 300). More particularly, the end cap 388 of the embodiment illustrated includes a protuberance 388a facing inward for mounting an annular magnet 372 thereon. Like the tattoo machine 200, the magnet 372 in the tattoo machine 300 is arranged opposite another magnet 376 in the tattoo machine 300. It is to be appreciated that the magnets 372, 376 need not be annular and that the exact arrangement by which the magnets are cooperatively mounted within the tattoo machine 300 may vary.

As shown, a set screw 382 secures and locks a position of the end cap 388 and thereby the magnet 372 within the tattoo machine 300. As shown in the illustrated embodiment, the set screw 382 can be received in a slot 388b of the end cap 388 that limits an amount of axial adjustment allowed for the end cap 388, though this is not required. To adjust the end cap 388 and change the position of the magnet 372, the set screw 382 is loosened via an appropriate tool (e.g., hex head tool), the end cap 388 moved to a desired position, and the set screw 382 re-tightened. Notably, the set screw 382 cannot be loosened when a tattoo tube 14 is installed in the tattoo machine 300. Accordingly, adjustments to the position of the end cap 388 and the magnet 372 carried thereby are only enabled when there is no tattoo tube 14 installed in the tattoo machine.

Figure 6:
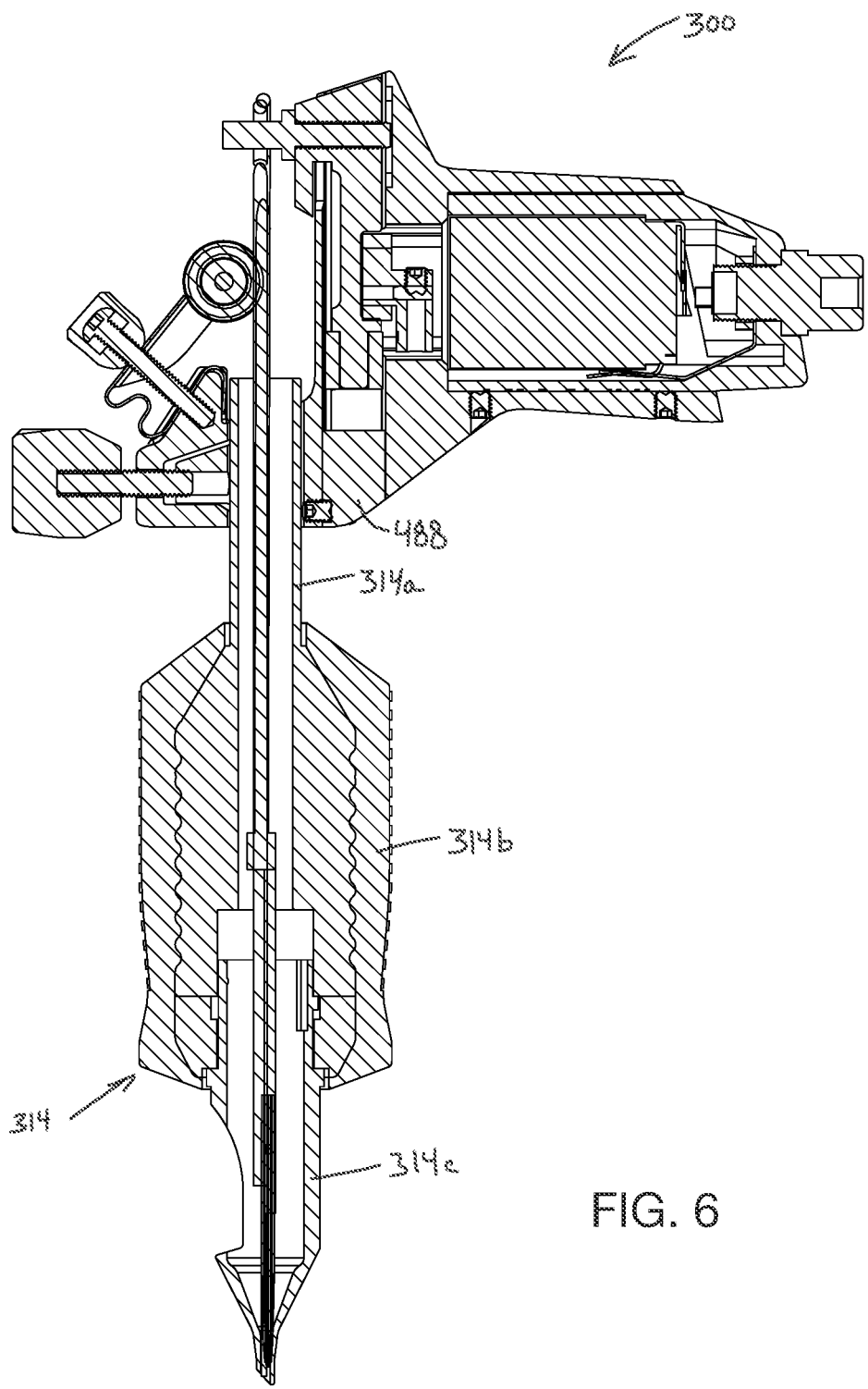
FIG. 6 is similar to FIG. 5 and shows the same tattoo machine but shows a plug replacing the end cap and magnet for enabling the tattoo machine to be used with cartridge type tattoo needles.

With reference to now to FIG. 6, the tattoo machine 300 is shown with a cartridge style tattoo needle assembly 314 installed in the tattoo machine. As is known and understood by those skilled in the art, the cartridge style tattoo needle assembly 314 includes a tube 314a that can be installed in the tattoo machine 300 in the same manner as tattoo tube 14, a grip 314b for holding during operation of the tattoo machine, and a needle cartridge 314c removably received in the grip 314b. As the cartridge style tattoo needle assembly 314 includes a resilient device internally (e.g., a resilient diaphragm), magnetic dampening within the tattoo machine 300 is generally not desired. Accordingly, the magnet 372 and end cap 388 shown in FIG. 5 can be removed and replaced with an end cap 488. In one embodiment, the end cap 488 is an inert plastic plug that functions to prevent contaminants from entering the tattoo machine 300 and maintains aesthetics on the exterior of the tattoo machine 300 (i.e., no open aperture is exposed as would occur if the end cap 388 were simply removed and not replaced).

A method of dampening a tattoo machine will now be described. In particular, the method will be described in association with the tattoo machine 10 of FIGS. 1-3, though it is to be appreciated by those skilled in the art that the method could be used with other tattoo machines. In the method, a main housing 16, a motor 18 and a needle bar member 20 are all provided. The motor 18 is secured to the main housing 16. The needle bar member 20 is movably secured to the main housing 16 for linear oscillation relative thereto. A drive mechanism 30, 32 is arranged on the main housing 16 to translate rotary motion of the output shaft 26 of the motor 18 into linear oscillation of the needle bar member 20. The drive mechanism 30, 32 can include an eccentric member 30 and a cartridge 32 comprised of the primary piston 40 and the secondary piston 42. The eccentric member 30 drives or reciprocates the piston 40 linearly along an axis thereof as the motor 18 rotates the eccentric member 30. In particular, the piston 40 reciprocate the needle bar member 20 via the secondary piston 42 (in contrast, piston 40' directly reciprocates the needle bar member 20).

In the method, the linear oscillation of the needle bar member 20 can be dampened with a pair of magnets. For example, the pair of magnets 70, 72 can be provided at a lower end of the machine 10 for dampening extended movement of the needle 12 and/or the pair of magnets 74, 76 can be provided at the upper end of the tattoo machine 10 for dampening retracted movement of the needle 12. Additionally, such dampening provided by the magnets can be adjusted by moving a first one of the pair of magnets relative to a second one of the pair of magnets. For example, the magnet 72 can move relative to the magnet 70 and/or the magnet 76 can move relative to the magnet 74, particularly when or the tattoo machine 10 is not in use or between uses. Also, the motor 18 can be removed via a magnetic connection (e.g., between magnets 122 and 124) between a motor housing 120 to which the motor 18 is fixed in the main housing 16.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A tattoo machine for oscillating a tattoo needle, comprising:
   a main housing;
   a motor secured to the main housing;
   a needle bar member movably secured to the main housing for linear oscillation relative thereto;
   a drive mechanism operatively connected to an output shaft of the motor and to the needle bar member for translating rotary movement of the output shaft into linear oscillation of the needle bar member, wherein the drive mechanism includes:
      an eccentric member fixed to the output shaft of the motor for rotation therewith, and
      a cartridge operatively connected to the needle bar member and having a slot defined therein for complementarily receiving the eccentric member such that rotary movement of the eccentric member linearly oscillates the cartridge and thereby the needle bar member; and
   a pair of magnets disposed axially within the main housing at one end of the cartridge for dampening oscillating movement of the cartridge and thereby the needle bar member, the pair of magnets including a first magnet and a second magnet, the first magnet arranged for synchronous movement with the cartridge and the second magnet mounted to the main housing, wherein an axial distance is defined between the pair of magnets when the cartridge is at rest, said axial distance is adjustable while the cartridge is at rest, and wherein the second magnet is adjustably movable relative to the main housing for adjusting said axial distance between the pair of magnets.

2. The tattoo machine of claim 1, wherein the cartridge includes:
   a primary piston having the slot defined therein; and
   a secondary piston slidably and nestably received within an axial recess defined within one end of the primary piston, the needle bar member fixed to the secondary piston for synchronized movement therewith.

3. The tattoo machine of claim 1, wherein the second magnet is prevented from adjustment when a tattoo tube is installed and secured to the main housing.

4. The tattoo machine of claim 1, wherein the pair of magnets are disposed at a lower end of the cartridge for dampening extended movement of the needle bar member.

5. The tattoo machine of claim 4, wherein the pair of magnets is a first pair of magnets and the tattoo machine further includes:

a second pair of magnets disposed axially within the main housing at an upper end of the cartridge for dampening retracted movement of the needle bar member.

6. The tattoo machine of claim 5, wherein another axial distance is defined between the second pair of magnets when the cartridge is at rest, and wherein said another axial distance is adjustable.

7. The tattoo machine of claim 1, wherein the cartridge includes:
a primary piston to which the needle bar member is fixed for synchronized movement therewith.

8. The tattoo machine of claim 7, wherein the cartridge further includes:
a sleeve member in which the primary piston is received, the sleeve member having an axially oriented sleeve slot through which the needle bar member extends and a cutout portion defined therein along which a cut-out portion of the primary piston slidably travels.

9. The tattoo machine of claim 1, wherein the motor is fixedly secured within a motor housing that is removably secured to the main housing thereby allowing the motor housing and the motor to be selectively detached from the main housing.

10. The tattoo machine of claim 9, wherein the motor housing is removably secured to the main housing by at least one magnetic connection.

11. A tattoo machine for oscillating a tattoo needle, comprising:
a main housing;
a motor secured to the main housing;
a needle bar member movably secured to the main housing for linear oscillation relative thereto; and
a drive mechanism operatively connected to an output shaft of the motor and to the needle bar member for translating rotary movement of the output shaft into linear oscillation of the needle bar member, wherein the drive mechanism includes an eccentric member fixed to the output shaft of the motor for rotation therewith and a cartridge operatively connected to the needle bar member and having a slot defined therein for complementarily receiving the eccentric member such that rotary movement of the eccentric member linearly oscillates the cartridge and thereby the needle bar member, wherein the cartridge includes a primary piston having the slot defined therein and a secondary piston slidably and nestably received within an axial recess defined within one end of the primary piston, the needle bar member fixed to the secondary piston for synchronized movement therewith,
and further wherein the primary piston includes a base wall defining a depth of the axial recess, the base wall configured to abut one end of the secondary piston when the eccentric member moves the primary piston in a first direction toward the secondary piston and is configured to move the secondary piston in said first direction with said primary piston.

12. The tattoo machine of claim 11, wherein the primary piston includes a side wall defining a circumference of the axial recess, the side wall defining an axially oriented slot through which at least one of the secondary piston and the needle bar member is received, end portions of the side wall defining the axially oriented slot are configured to limit oscillating movement of the secondary piston and the needle bar member relative to the primary piston.

13. The tattoo machine of claim 12, wherein the cartridge further includes a sleeve member in which the primary piston is received, the sleeve member having an axially oriented sleeve slot defined therein along which the axially oriented slot defined in the primary piston slidably travels, and the sleeve member having a cutout portion defined therein along which a cut-out portion of the primary piston slidably travels.

* * * * *